(12) United States Patent
Kim

(10) Patent No.: US 10,194,869 B2
(45) Date of Patent: Feb. 5, 2019

(54) APPARATUS AND METHOD FOR MEASURING BIOSIGNALS

(71) Applicant: SAMSUNG ELECTRONICS CO., LTD., Suwon-si (KR)

(72) Inventor: Jong Pal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 279 days.

(21) Appl. No.: 14/049,523

(22) Filed: Oct. 9, 2013

(65) Prior Publication Data

US 2014/0121565 A1   May 1, 2014

(30) Foreign Application Priority Data

Oct. 29, 2012 (KR) .................. 10-2012-0120151

(51) Int. Cl.
| | | |
|---|---|---|
| *A61B 5/00* | (2006.01) | |
| *A61B 5/0428* | (2006.01) | |
| *A61B 5/0452* | (2006.01) | |
| *A61B 5/04* | (2006.01) | |
| *A61B 5/11* | (2006.01) | |

(52) U.S. Cl.
CPC ........ *A61B 5/7207* (2013.01); *A61B 5/04017* (2013.01); *A61B 5/0428* (2013.01); *A61B 5/0452* (2013.01); *A61B 5/11* (2013.01); *A61B 5/7214* (2013.01); *A61B 5/7221* (2013.01); *A61B 2560/0209* (2013.01); *A61B 2560/0247* (2013.01); *Y10S 128/901* (2013.01)

(58) Field of Classification Search
CPC ..... A61B 5/7207; A61B 5/721; A61B 5/7214; A61B 5/7203; A61B 5/7235; A61B 5/7246; A61B 5/04012; A61B 5/04028; A61B 5/0402; A61B 5/0428; A61B 5/0452–5/0472; A61B 2560/0247; Y10S 128/901
USPC ......................... 600/509, 513, 547
See application file for complete search history.

(56) References Cited

U.S. PATENT DOCUMENTS

| | | | |
|---|---|---|---|
| 5,226,417 A | 7/1993 | Swedlow et al. | |
| 5,978,693 A | 11/1999 | Hamilton et al. | |
| 7,072,708 B1 | 7/2006 | Andresen et al. | |
| 7,245,961 B2 * | 7/2007 | Blakley ................ | A61B 5/0428 600/509 |
| 7,684,856 B2 * | 3/2010 | Virtanen ............ | A61B 5/04004 600/544 |

(Continued)

FOREIGN PATENT DOCUMENTS

| | | |
|---|---|---|
| CN | 1722976 A | 1/2006 |
| CN | 102283641 A | 12/2011 |

(Continued)

OTHER PUBLICATIONS

Ghanem, et al. "Comparison of laplacian and bipolar ECGs for R-wave detection during noise." Engineering in Medicine and Biology Society, 2006. EMBS'06. 28th Annual International Conference of the IEEE. Abstract.*

(Continued)

*Primary Examiner* — David J. McCrosky
(74) *Attorney, Agent, or Firm* — NSIP Law

(57) ABSTRACT

An apparatus and method for measuring a biosignal that include generating a control signal for processing the biosignal based on an obtained replication signal or a sensed motion of the subject.

15 Claims, 7 Drawing Sheets

(56) References Cited

U.S. PATENT DOCUMENTS

| | | | |
|---|---|---|---|
| 8,583,225 B2* | 11/2013 | Lim | A61B 5/0531 600/547 |
| 8,855,753 B2* | 10/2014 | Kim | A61B 5/0408 128/901 |
| 2004/0049120 A1 | 3/2004 | Cao et al. | |
| 2006/0149146 A1 | 7/2006 | Schmidt et al. | |
| 2007/0142735 A1 | 6/2007 | Shin et al. | |
| 2007/0173734 A1 | 7/2007 | Kim et al. | |
| 2011/0130672 A1 | 6/2011 | Kim et al. | |
| 2012/0004563 A1 | 1/2012 | Kim et al. | |
| 2012/0123226 A1 | 5/2012 | Schwenk et al. | |

FOREIGN PATENT DOCUMENTS

| | | |
|---|---|---|
| EP | 1 795 122 A1 | 6/2007 |
| EP | 2 394 571 A1 | 12/2011 |
| JP | 05-003860 A | 1/1993 |
| JP | 05-154120 A | 6/1993 |
| JP | 11-318842 A | 11/1999 |
| JP | 2009-112625 A | 5/2009 |
| KR | 10-2006-0119472 A | 11/2006 |
| KR | 10-2010-0067363 A | 6/2010 |
| KR | 10-1029386 B1 | 4/2011 |
| KR | 10-2011-0106340 A | 9/2011 |

OTHER PUBLICATIONS

Devlin, et al. "Detection electrode motion noise in ecg signals by monitoring electrode impedance." Computers in Cardiology (1984): 51-56.*

Hamilton, et al. "Comparison of methods for adaptive removal of motion artifact." Computers in Cardiology 2000. pp. 383-386.*

Widrow, Bernard, et al. "Adaptive noise cancelling: Principles and applications," *Proceedings of the IEEE*, vol. 63, No. 12, Dec. 1975, pp. 1692-1716.

Extended European Search Report dated Feb. 19, 2014 in counterpart European Patent Application No. 13185852.4. (12 pages in English)

Chinese Office Action dated Mar. 25, 2016 in counterpart Chinese Patent Application No. 201310438795.X (28 pages in Chinese with English translation).

* cited by examiner

400

APPARATUS AND METHOD FOR MEASURING BIOSIGNALS

CROSS-REFERENCE TO RELATED APPLICATION(S)

This application claims the benefit under 35 U.S.C. § 119(a) of Korean Patent Application No. 10-2012-0120151, filed on Oct. 29, 2012, in the Korean Intellectual Property Office, the entire disclosure of which is incorporated herein by reference for all purposes.

BACKGROUND

1. Field

The following description relates to an apparatus and method for measuring bio signals.

2. Description of Related Art

Various medical systems are typically used and various medical tests are typically performed for conducting a medical diagnosis of a patient. It is often very important to measure electrical biosignals of a patient, including an electrocardiogram (ECG), a brain wave or electroencephalogram (EEG), an electromyogram (EMG), and the like. The measurement of biosignals generally provides greater convenience to a patient during a medical diagnostic process and quicker results of the medical diagnosis. Since biosignals have characteristics of electrical signals, measuring such biosignals accurately without artifacts is important.

SUMMARY

In one general aspect, there is provided an apparatus for measuring a biosignal that may include a motion artifact, the apparatus including: a measuring module configured to measure the biosignal; an obtaining module configured to obtain a replication signal; and a control module configured to generate a control signal, based on the replication signal, for controlling processing of the biosignal.

The obtaining module may be further configured to measure a change in impedance between electrodes used by the measuring module in measuring the bio signal, or a change in a half cell potential to obtain the replication signal, and the replication signal may be similar to the motion artifact.

The control module may be further configured to determine whether the biosignal is to be processed based on a degree of the motion artifact relating to the replication signal and generate the control signal based on a result of the determining.

The control module may include an indexing unit configured to index a value based on a degree of the motion artifact relating to the replication signal; a determining unit configured to compare the indexed value to a threshold value; and a generating unit configured to generate the control signal based on a result of the determining.

The indexed value may be a distribution of the replication signal, a root mean square of the replication signal, or an average magnitude of the replication signal during a time period.

The apparatus may further include a signal processing module configured to process the biosignal based on the control signal by filtering the biosignal for reducing the motion artifact.

The apparatus may further include a signal processing module configured to process the biosignal by filtering the biosignal using the replication signal, or not process the biosignal, based on the control signal.

In another general aspect, there is provided an apparatus for measuring a biosignal that may include a motion artifact, the apparatus including: a measuring module configured to measure the biosignal; a sensing module configured to sense a motion of the subject; and a control module configured to generate a control signal, based on the sensed motion, for controlling processing of the biosignal.

The sensing module may use an inertial sensor for sensing the motion, the apparatus may further include a signal processing module configured to process the biosignal based on the control signal, and the control module may include a determining unit configured to determine whether the biosignal is to be processed based on a degree of the motion artifact relating to the sensed motion, and a generating unit configured to generate the control signal based on a result of the determining.

The control signal may be a first control signal, the generating unit may be a first generating unit, the apparatus may further include an obtaining module configured to obtain a replication signal that is similar to the motion artifact, and the control module may further include a second generating unit configured to generate a second control signal, based on a result of the determining, for operating the obtaining module.

The control module may further include an indexing unit configured to index a value based on the degree of the motion artifact, and the determining unit may be configured to compare the indexed value to a threshold value to determine whether the motion artifact is to be processed.

The indexed value may be a magnitude or a root mean square of an average acceleration of the sensed motion during a time period.

In another general aspect, there is provided a method of measuring a biosignal that may include a motion artifact, the method including: measuring the biosignal, obtaining a replication signal, and generating a control signal, based on the replication signal, for controlling processing of the biosignal.

The obtaining may include measuring a change in impedance between electrodes used by the measuring module in measuring the bio signal, or a change in a half cell potential to obtain the replication signal, and the replication signal may be similar to the motion artifact.

The generating may include determining whether the biosignal is to be processed based a degree of the motion artifact relating to the replication signal, and generating the control signal based on a result of the determining.

The generating may further include indexing a value based on a degree of the motion artifact relating to the replication signal, comparing the indexed value to a threshold value, and generating the control signal based on a result of the determining.

The indexed value may be a distribution of the replication signal, a root mean square of the replication signal, or an average magnitude of the replication signal during a time period.

The method may further include processing the biosignal based on the control signal by filtering the biosignal for reducing the motion artifact.

The method may further include processing the biosignal by filtering the biosignal using the replication signal, or not processing the biosignal, based on the control signal.

In another general aspect, there is provided a non-transitory computer-readable storage medium storing a program for controlling a computer to execute the method In another general aspect, there is provided a method of measuring a biosignal that may include a motion artifact, the method including: measuring the biosignal; sensing a motion of the subject; and generating a control signal, based on the sensed motion, for controlling processing of the biosignal.

The sensing module may use an inertial sensor for sensing the motion, the method may further include processing the biosignal based on the control signal, and the generating may include determining whether the biosignal is to be processed based on a degree of the motion artifact relating to the sensed motion, and generating the control signal for controlling processing of the biosignal based on a result of the determining.

The control signal may be a first control signal, and the method further include obtaining a replication signal that is similar to the motion artifact, and generating a second control signal, based on a result of the determining, for obtaining the replication signal.

The generating may further include indexing a value based on the degree of the motion artifact, the determining may include comparing the indexed value to a threshold value to determine whether the motion artifact is to be processed.

The indexing may include indexing a magnitude or a root mean square of an average acceleration according to the sensed motion during a time period.

DETAILED DESCRIPTION

Figure 1:
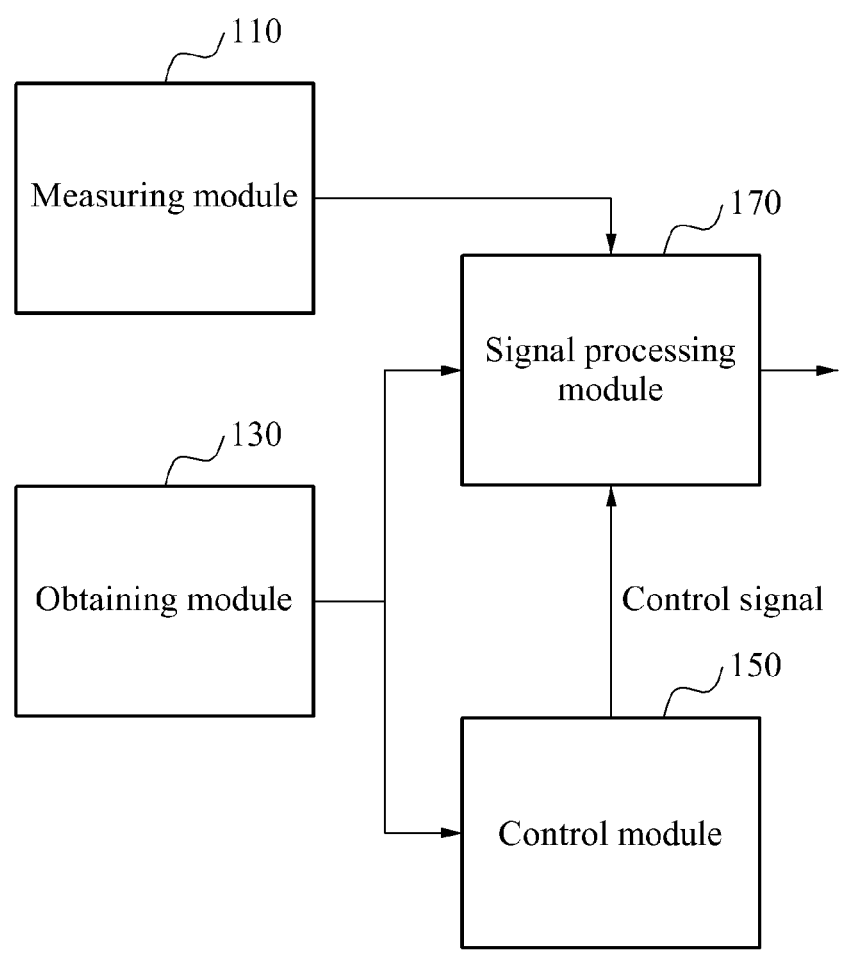
FIG. 1 is a block diagram illustrating an example of an apparatus for measuring a biosignal.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 illustrates an example of a measuring apparatus 100 for measuring a biosignal. Referring to FIG. 1, the measuring apparatus 100 includes a measuring module 110, an obtaining module 130, a control module 150, and a signal processing module 170.

The measuring module 110 may measure a biosignal of a subject, for example, an electrocardiogram (ECG), an electroencephalogram (EEG), an electromyogram (EMG), and the like.

In an example, the biosignal of the subject may be measured by a potential difference or voltage between a pair of interfaces or electrodes. The biosignal of the subject may be measured by a potential at a single point using a single interface or may be measured by a combination of values detected by more than one interface.

In this example, the measuring module 110 includes an interface to be in physical contact with a surface of the subject in order to measure the biosignal of the subject. Due to the subject moving continuously, or as a result of the electrode being out of a set measurement point, impedance between the subject and the electrode may inevitably be changed. Such a change in the impedance acts as noise or a motion artifact with respect to a biosignal collected by the measuring module 110. This causes measurement interference or waveform distortion with respect to a measuring result.

Referring to FIG. 1, the measuring module 110 provides the biosignal of the subject, including the motion artifact, to the signal processing module 170. The obtaining module 130 obtains a replication signal similar to the motion artifact. For example, the obtaining module 130 obtains the replication signal using a scheme of measuring a change in impedance between electrodes. In another example, the obtaining module 130 obtains the replication signal using a change in a half cell potential.

An example of a method by which the obtaining module 130 obtains the replication signal using the scheme of measuring the change in impedance is as follows. An electrical cardiac signal having a signal component in a frequency band ranging from about 0.5 hertz (Hz) to 250 Hz may be differentially measured using a first electrode and a second electrode. Information about a change in impedance between the first electrode and the second electrode may be obtained by passing a sine-wave current through the first electrode and the second electrode, differentially measuring a voltage formed at the first electrode and the second electrode, and demodulating the differentially measured voltage into a signal of 2 kilohertz (kHz). The obtained information replicates a motion artifact signal included in the ECG signal.

An example of a method by which the obtaining module 130 obtains the replication signal using the scheme of measuring a change in the half cell potential is as follows. The obtaining module 130 receives the biosignal of the subject from interfaces A and B, being in contact with the skin of the subject, or from the measuring module 110. The obtaining module 130 also detects a dummy signal from dummy interfaces Ad and Bd having electrical characteristics differing from electrical characteristics of the interfaces A and B. The obtaining module 130 extracts a signal proportional to the motion artifact from the biosignal of the subject and the dummy signal. In this instance, the extracted signal proportional to the artifact is the replication signal.

In this example, in order to remove the motion artifact included in the biosignal of the subject, the motion artifact is traced using the dummy signal detected by the dummy interfaces Ad and Bd. That is, a change in the dummy signals detected by the dummy interfaces Ad and Bd due to the subject's motion, should be similar to the change in the signals detected by the interfaces A and B due to the subject's motion.

Accordingly, the interface A and the dummy interface Ad are disposed close to one another and within a threshold distance. This allows for an almost identical external artifact change factor for the interface A and the dummy interface Ad. For example, the threshold distance may be set to 1 centimeter (cm) or 1 millimeter (mm).

Similarly, the interface B and the dummy interface Bd are disposed close to one another. In this example, the interface A and the interface B are disposed a distance apart from each other. This distance is sufficient for detecting the biosignal of the subject, in particular, the voltage between the interface A and the interface B.

When the interface A and the dummy interface Ad are disposed close to each other, motions of electrodes of the interface A and the dummy interface Ad resulting from the motion of the subject are almost identical. Accordingly, a change in the electrical characteristic of the interface A and a change in the electrical characteristic of the dummy interface Ad caused by an external factor, such as the motion of the subject, have similar aspects.

In this example, the obtaining module 130 uses the similarity in the electrical characteristic change between the interface A and the dummy interface Ad and the similarity in the electrical characteristic change between the interface B and the dummy interface Bd. Accordingly, the obtaining module 130 extracts an artifact signal proportional to the motion artifact included in the biosignal of the subject using the signals detected by the interface A, the interface B, the dummy interface Ad, and the dummy interface Bd.

For example, the obtaining module 130 extracts the replication signal using a similarity in a voltage change between voltage sources in an equivalent circuit of each of the interface A and the dummy interface Ad and a similarity in a voltage change between voltages sources in an equivalent circuit of each of the interface B and the dummy interface Bd.

Referring to FIG. 1, the replication signal obtained by the obtaining module 130, which is similar to the motion artifact, is provided to the control module 150 and the signal processing module 170.

In this example, the control module 150 generates a control signal for processing the motion artifact, based on the degree of the motion artifact as expressed in the replication signal. The control module 150 determines whether the motion artifact is to be processed, based on the artifact degree relating to the replication signal provided from the obtaining module 130, and may generate a control signal for processing the motion artifact based on a result of the determining.

For example, the control module 150 indexes a motion artifact signal using the artifact degree. When it is determined that the indexed motion artifact signal is great enough to exceed a predetermined threshold, the control module 150 generates a control signal for controlling the signal processing module 170 to perform signal processing with respect to the motion artifact. When it is determined that the motion artifact is absent or the artifact degree is modest since the indexed motion artifact signal does not exceed the predetermined threshold, the control module 150 controls the signal processing module 170 to omit the signal processing task for removing the motion artifact. In this example, the signal processing module 170 processes the motion artifact included in the biosignal of the subject, based on the control signal generated by the control module 150. The signal processing module 170 performs filtering for reducing the motion artifact included in the biosignal of the subject based on the control signal.

For example, the signal processing module 170 reduces the motion artifact included in the biosignal of the subject using an adaptive filter. An adaptive filter includes a digital filter capable of adjusting filter coefficients based on values fed back to the filter. In this example, the signal processing module 170 removes the motion artifact from the biosignal by adjusting filter coefficients based on the replication signal obtained by the obtaining module 130. The biosignal, corresponding to a voltage waveform between the interface A and the interface B, is filtered using the adjusted filter coefficients.

For example, the signal processing module 170 may perform signal processing, as initiated by the control signal, by filtering out the motion artifact from the biosignal. When the signal processing module 170 performs signal processing a result of the signal processing is output by the signal processing module 170. On the other hand, when the control signal disallows the processing of the motion artifact, the signal processing module 170 omits the signal processing task.

By controlling the signal processing module 170 to omit the signal processing for removing the motion artifact when the motion artifact is absent, the measuring apparatus 100 is able to reduce power consumption. That is, the measuring apparatus is able to selectively perform signal processing, such as filtering using an adaptive filter, when the motion artifact is determined to exist.

For example, a difference in power consumption between a case in which the adaptive filter performs the operation and a case in which the adaptive filter omits the operation may correspond to 100 microamperes ($\mu$A). In addition, when an ECG sensor as an example of the measuring apparatus is worn, a ratio of an inoperative state to an operational state of the signal processing module 170 may correspond to a ratio of about 9:1. In this example, an average current consumption for the operation of the adaptive filter in the signal processing module 170 may be reduced from 100 $\mu$A to 10 $\mu$A.

Figure 2:
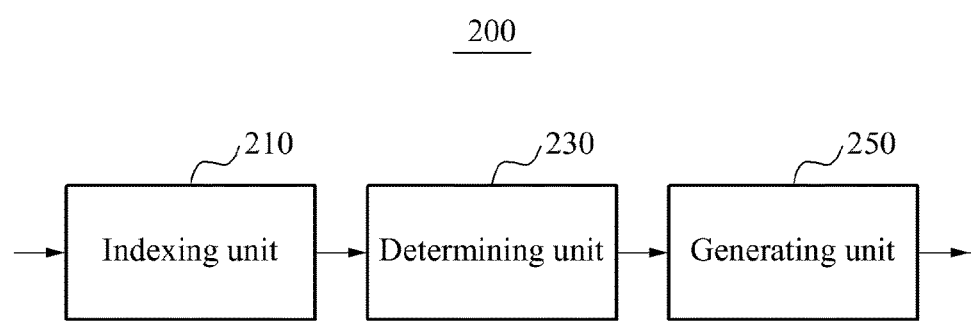
FIG. 2 is a block diagram illustrating an example of a control module of the measuring apparatus of FIG. 1.

FIG. 2 illustrates an example of a control module 200 of the measuring apparatus 100 of FIG. 1. Referring to FIG. 2, the control module 200 includes an indexing unit 210, a determining unit 230, and a generating unit 250.

In this example, the indexing unit 210 indexes an artifact degree of a motion artifact included in a biosignal, based on the replication signal provided by the obtaining module 130. The indexing unit 210 indexes a distribution, a root mean square (rms), or an average size of the replication signal during a predetermined time period as the artifact degree. For example, the predetermined period of time may be one second.

In this example, the control module 200 also includes a determining unit 230. The determining unit 230 compares a value indexed by the indexing unit 210 to a predetermined threshold value to determine whether the motion artifact is to be processed. For example, the determining unit 230 determines that filtering for removing the motion artifact is necessary when the indexed value exceeds the predetermined threshold value. In addition, the determining unit 230 determines to omit the filtering when it is determined that the indexed value does not exceed the predetermined threshold value and a motion artifact to be removed is absent. Accordingly, when a motion artifact to be removed is absent, the filtering is omitted and power consumption is reduced.

In this example, the control module 200 also includes a generating unit 250. The generating unit 250 generates a control signal for operating the signal processing module 170 based on a result of the determining performed by the determining unit 230.

Figure 3:
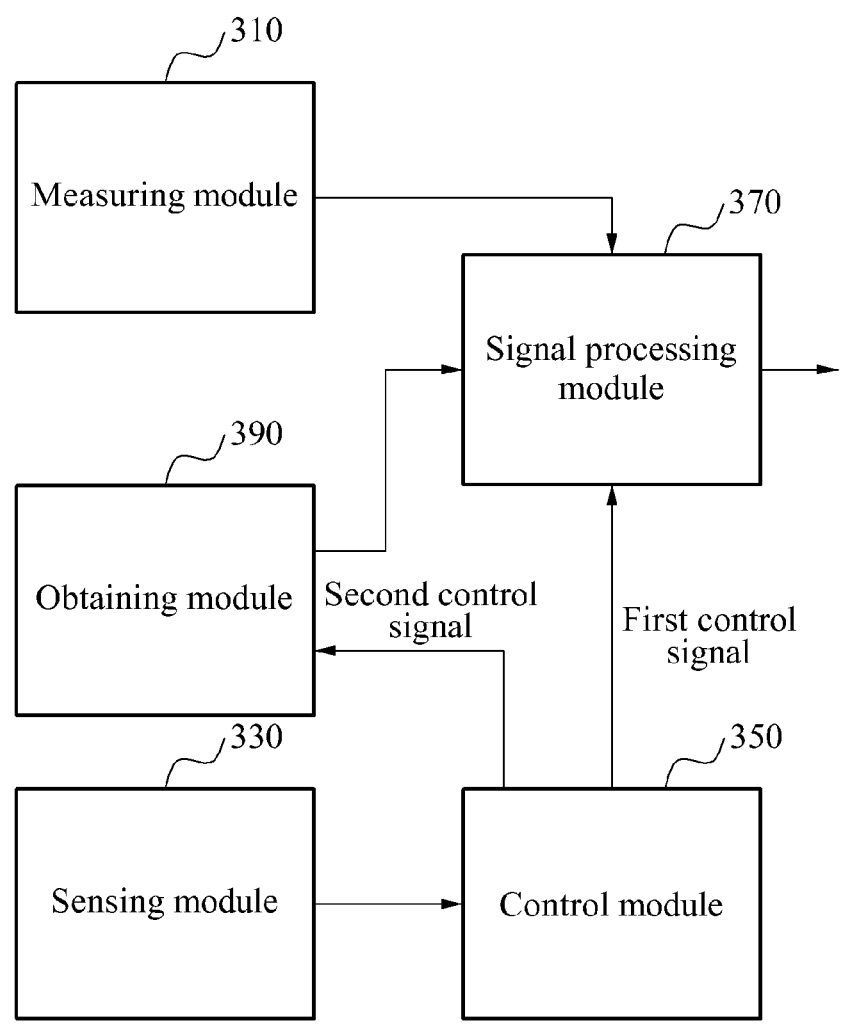
FIG. 3 is a block diagram illustrating another example of an apparatus for measuring a biosignal.

FIG. 3 illustrates another example of an apparatus 300 for measuring a biosignal. Referring to FIG. 3, the measuring apparatus 300 includes a measuring module 310, a sensing module 330, a control module 350, a signal processing module 370, and an obtaining module 390.

The measuring module 310 measures a biosignal of a subject including a motion artifact occurring in an interface when the biosignal is measured. The sensing module 330 senses a motion of the subject using an inertial sensor such as an accelerometer, a gyroscope, or the like. For example, to determine artifact degree using the accelerometer, the sensing module 330 uses the magnitude of acceleration in all directions or axes, and extracts and uses information on a height direction of the user. The sensing module 330 provides information related to the sensed motion of the subject to the control module 350.

The control module 350 generates a control signal for controlling the processing of the motion artifact. In an example, the control module 350 generates a first control signal based on the artifact degree received from the sensing module 330. A configuration and an operation of the control module 350 will be described in detail with reference to FIG. 4.

The signal processing module 370 processes the motion artifact included in the biosignal of the subject based on the first control signal generated by the control module 350. In this example, the signal processing module 370 processes the motion artifact using a replication signal obtained by the obtaining module 390. The description provided with reference to FIG. 1 may be referred to with respect to a method by which the signal processing module 370 may process the motion artifact using the replication signal.

The obtaining module 390 is operated based on a second control signal that is generated by the control module 350 based on an artifact degree. In order to reduce a power consumption of the obtaining module 390, the measuring apparatus 300 controls the operation of the obtaining module 390. The obtaining module 390 may be signaled to operate only when the artifact degree of the motion artifact, based on the motion of the subject, is relatively high.

Figure 4:
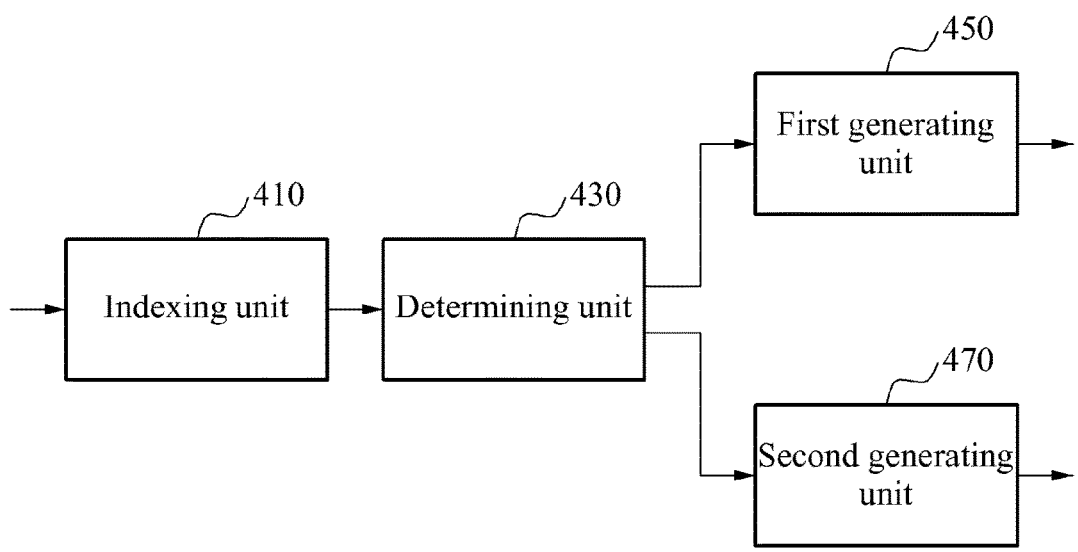
FIG. 4 is a block diagram illustrating an example of a control module of the measuring apparatus of FIG. 3.

FIG. 4 illustrates an example of a control module 400 of the measuring apparatus 300 of FIG. 3. Referring to FIG. 4, the control module 400 includes an indexing unit 410, a determining unit 430, a first generating unit 450, and a second generating unit 470.

The indexing unit 410 indexes an artifact degree of a motion artifact based on a motion of a subject. The indexing unit 410 indexes the artifact degree based on the magnitude of average acceleration for a predetermined time period or a root mean square (rms) magnitude of the average acceleration according to the motion of the subject.

In this example, the control module also includes a determining unit 430. The determining unit 430 determines whether the motion artifact is to be processed based on the artifact degree relating to the motion of the subject. The determining unit 430 compares the indexed value, which is the artifact degree, to a predetermined threshold value to determine whether the motion artifact is to be processed.

In this example, the control module also includes a first generating unit 450. The first generating unit 450 generates a first control signal for controlling the signal processing module 370 based on a result of the determining performed by the determining unit 430. In addition, the second generating unit 470 generates a second control signal for operating the obtaining module 390 based on the result of the determining performed by the determining unit 430.

Figure 5:
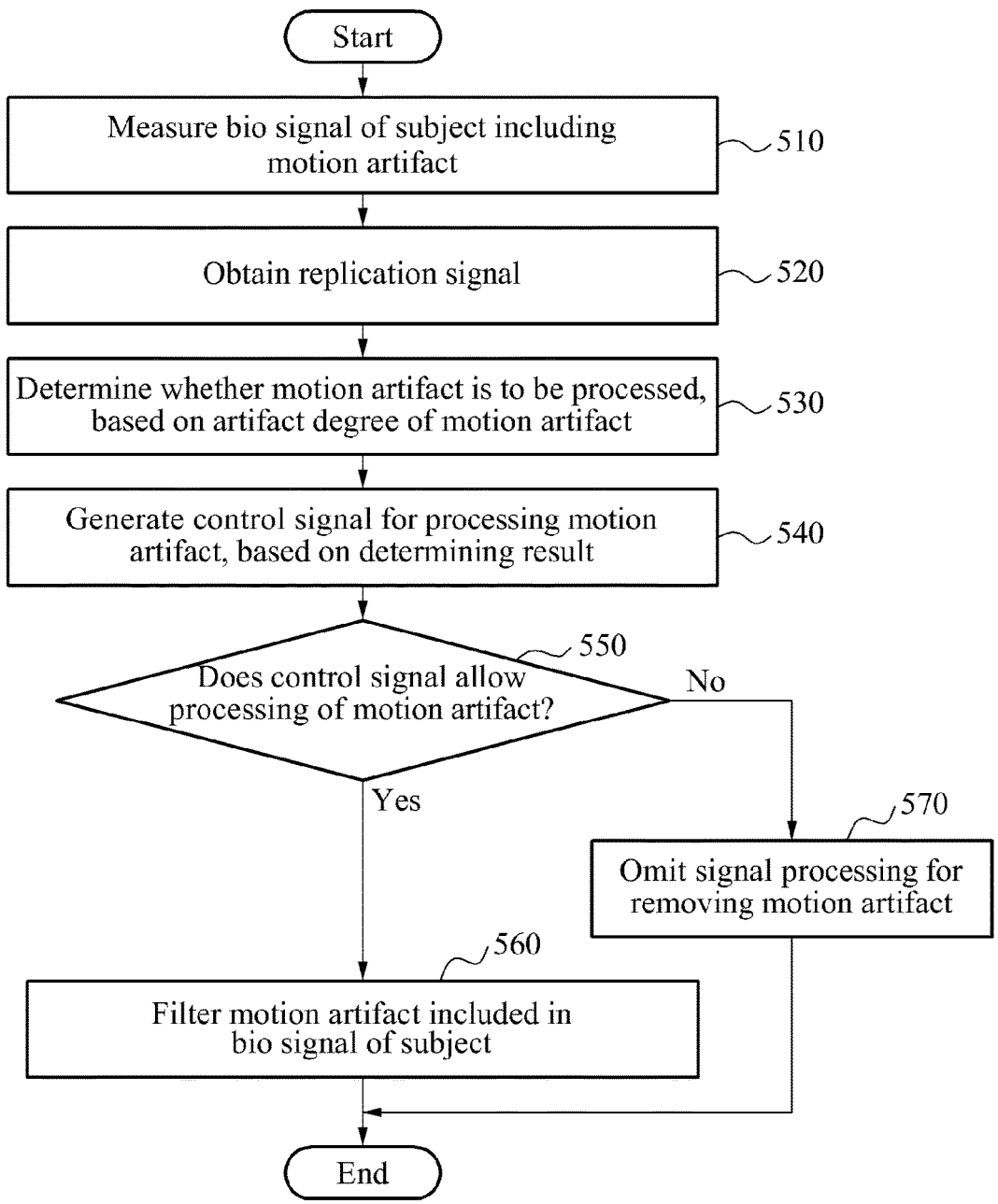
FIG. 5 is a flowchart illustrating an example of a method of measuring a biosignal.

FIG. 5 illustrates an example of a method of measuring a biosignal.

Referring to FIG. 5, in 510, a measuring apparatus measures a biosignal of a subject including the undesired motion artifact occurring in an interface when the biosignal is measured.

In 520, the measuring apparatus obtains a replication signal similar to the motion artifact. For example, the measuring apparatus may measure a change in impedance between electrodes measuring the biosignal or measure a change in a half cell potential to obtain the replication signal. The measuring apparatus generates a control signal for processing the motion artifact based on an artifact degree obtained in 520.

In 530, the measuring apparatus determines whether the motion artifact is to be processed based on the artifact degree. In 540, the measuring apparatus generates the control signal based on a result of the determining in 530.

In this example, the measuring apparatus processes the motion artifact included in the biosignal of the subject based on the control signal generated in 540. The measuring apparatus may perform filtering for reducing the motion artifact included in the biosignal of the subject.

In 550, the measuring apparatus determines whether the control signal allows processing of the motion artifact. If processing is allowed, the measuring apparatus filters the motion artifact using the replication signal and outputs a result of the filtering in 560.

On the other hand, if processing is disallowed, the measuring apparatus omits the signal processing for removing the motion artifact from the biosignal of the subject in 570.

Figure 6:
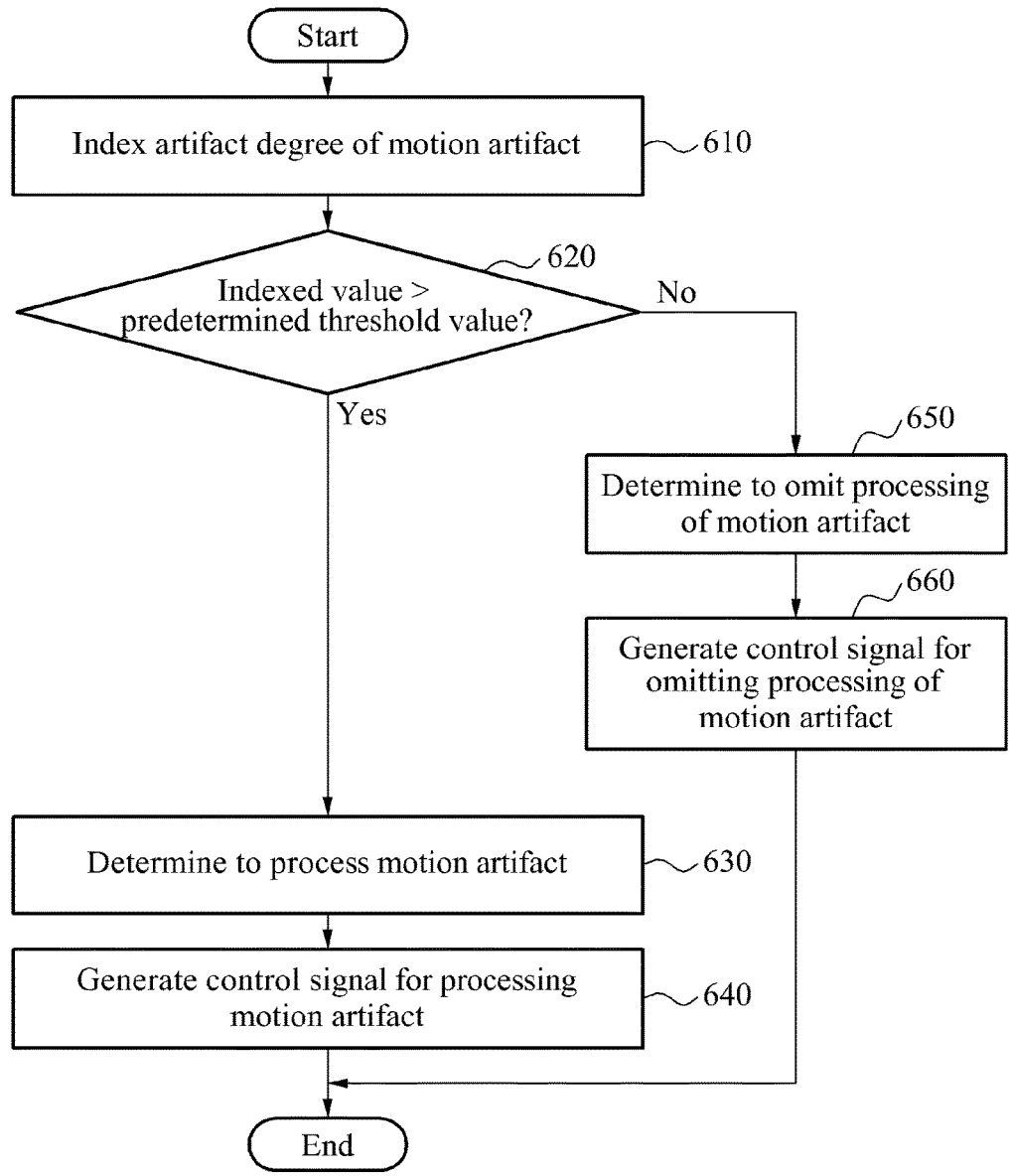
FIG. 6 is a flowchart illustrating an example of an operation of generating a control signal in a method of measuring a biosignal.

FIG. 6 illustrates an example of an operation of generating a control signal in a method of measuring a biosignal.

Referring to FIG. 6, in 610, a control module of a measuring apparatus indexes an artifact degree of a motion artifact based on a replication signal. The control module compares the indexed value to a predetermined threshold value. In 620, the control module determines whether the indexed value, that is the artifact degree, is greater than the predetermined threshold value.

When it is determined that the indexed artifact degree is greater than the predetermined threshold, the control module determines to process the motion artifact in 630, and generates a control signal for processing the motion artifact in 640. On the other hand, when it is determined that the indexed artifact degree of the motion artifact is less than or equal to the predetermined threshold value, the control module determines to omit processing of the motion artifact in 650, and generates a control signal for omitting the processing of the motion artifact in 660.

The method of measuring the biosignal described with reference to FIGS. 5 and 6 may consist of operations to be processed chronologically by the measuring apparatus of FIGS. 1 and 2. Accordingly, the description provided with reference to FIGS. 1 and 2 may be applied to the method described with reference to FIGS. 5 and 6.

Figure 7:
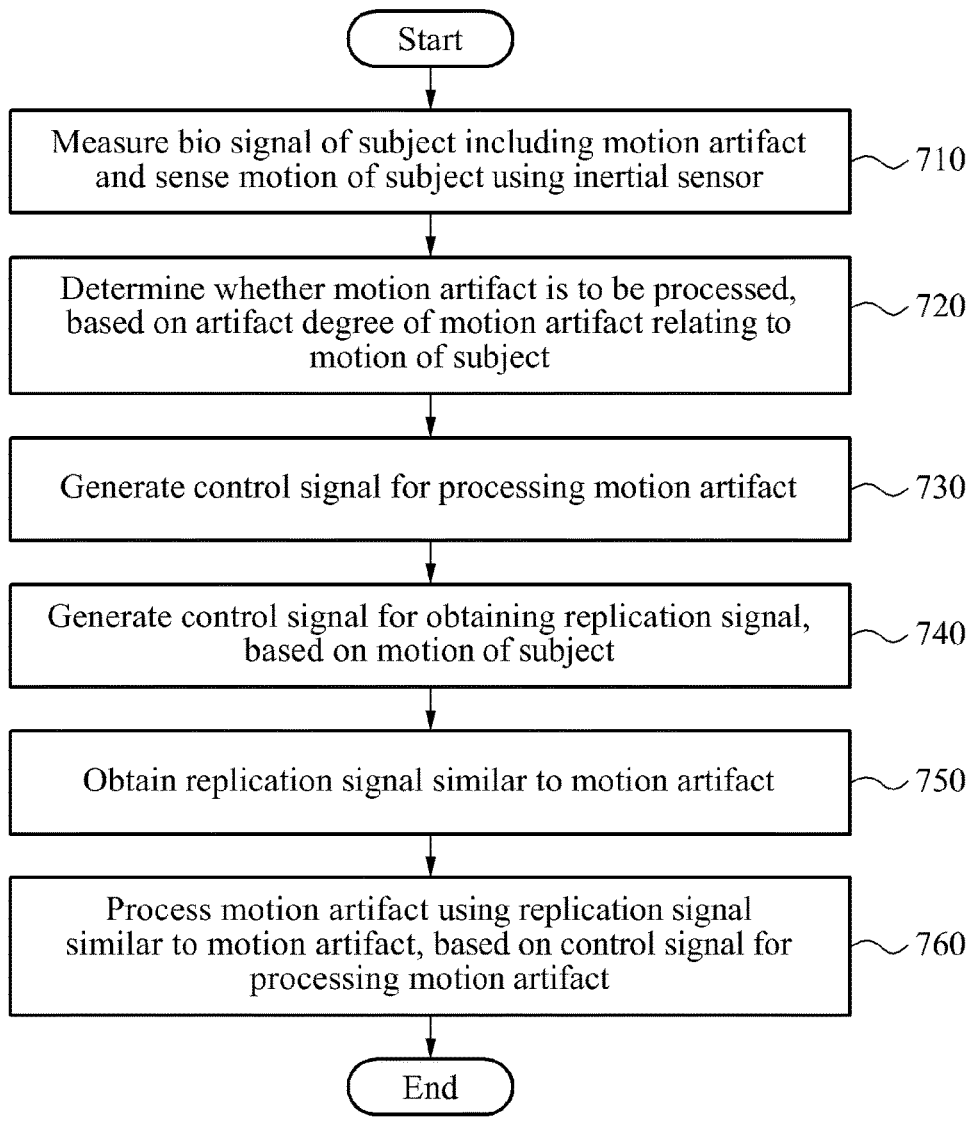
FIG. 7 is a flowchart illustrating another example of a method of measuring a biosignal.

FIG. 7 illustrates another example of a method of measuring a biosignal.

Referring to FIG. 7, a measuring apparatus may measure a biosignal of a subject including the undesired motion artifact occurring in an interface when the biosignal is measured. In 710, the measuring apparatus senses a motion of the subject using an inertial sensor such as an accelerometer, a gyroscope, or the like. In 710, the measuring of the biosignal of the subject and the sensing of the motion of the subject may be performed simultaneously or may be performed sequentially.

In this example, the measuring apparatus generates a control signal for processing the motion artifact based on the artifact degree relating to the sensed motion of the subject. In 720, the measuring apparatus determines whether the motion artifact is to be processed based on the artifact degree. In 730, the measuring apparatus generates a first control signal based on a result of the determining performed in 720.

In an example, the measuring apparatus generates the control signal based on an indexed artifact degree. The measuring apparatus indexes the artifact degree of the motion artifact based on the motion of the subject. For example, the measuring apparatus indexes the artifact degree based on a magnitude of an average acceleration during a predetermined time period. The measuring apparatus compares the indexed value to a predetermined threshold value to determine whether the motion artifact is to be processed. For example, when the indexed value is greater than the predetermined threshold value, the measuring apparatus may determine to perform filtering for removing the motion artifact. The measuring apparatus generates a control signal for processing the motion artifact based on a result of the determining as to whether the motion artifact is to be processed.

In 740, the measuring apparatus generates a second control signal for obtaining a replication signal similar to the motion artifact based on a result of the determining performed in 720. This may be performed after generating the first control signal or simultaneously. In 750, the measuring apparatus obtains the replication signal based on the second control signal generated in 740. In 760, the measuring apparatus processes the motion artifact included in the biosignal of the subject, using the replication signal, based on the control signal generated in 730.

The method of measuring the biosignal described with reference to FIG. 7 may consist of operations to be processed chronologically by the measuring apparatus of FIGS. 3 and 4. Accordingly, the description provided with reference to FIGS. 3 and 4 may be applied to the method described with reference to FIG. 7.

While the apparatus and method have been described for remotely managing a patient with a cardiac disease such as arrhythmia, other cardiac diseases may be managed based on the monitored ECG signal. Also, the apparatus and method may be used for monitoring and managing patients having other diseases by monitoring other types of biosignals. For example, musculoskeletal diseases may be managed by monitoring Electromyogram signals (EMG). Similarly, diseases related to brain activity may be managed by monitoring Electroencephalogram signals (EEG) or Magnetoencephalogram (MEG) signals. Also, Electrooculography (EOG) may be used to monitor ocular diseases and to Galvanic skin response (GSR) signals may be used to monitor skin diseases.

The measuring modules, obtaining modules, control modules, signal processing modules, and sensing modules described above may be implemented using one or more hardware components, or a combination of one or more hardware components and one or more software components. A hardware component may be, for example, a physical device that physically performs one or more operations, but is not limited thereto. Examples of hardware components include controllers, microphones, amplifiers, low-pass filters, high-pass filters, band-pass filters, analog-to-digital converters, digital-to-analog converters, and processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

Software or instructions for controlling a processing device, such as those described in FIGS. 5-7, to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for measuring a biosignal, the apparatus comprising:
   a biosignal interface configured to measure the biosignal;
   a dummy interface configured to detect a dummy signal;
   a processor configured to
      obtain a replication signal from the biosignal using the biosignal interface and the dummy interface,
      wherein the replication signal is proportional to a motion artifact in the biosignal;
      determine, based on the replication signal, an artifact degree of the motion artifact;
      compare the artifact degree to a threshold to generate a comparison result;
      generate, based on the comparison result, a control signal for controlling adaptive filtering of the biosignal to reduce the motion artifact; and
      process the biosignal based on the control signal.

2. The apparatus of claim 1, wherein the processor is configured to obtain the replication signal from the biosignal by
   measuring a change in a half cell potential between the biosignal interface and the dummy interface.

3. The apparatus of claim 1, wherein the processor is configured to determine the artifact degree by indexing the replication signal during a time period.

4. The apparatus of claim 3, wherein the processor is configured to index the replication signal by indexing a distribution of the replication signal, a root mean square of the replication signal, or an average magnitude of the replication signal during the time period.

5. The apparatus of claim 1, wherein the processor is configured to generate the control signal by:
   if the comparison result indicates that the artifact degree exceeds the threshold, generating the control signal to indicate that the adaptive filtering is to be performed; and
   if the comparison result indicates that the artifact degree does not exceed the threshold, generating the control signal to indicate that the adaptive filtering is not to be performed.

6. The apparatus of claim 5, wherein the processor is further configured to;
   if the control signal indicates that the adaptive filtering is to be performed, process the biosignal by performing the adaptive filtering on the biosignal to reduce the motion artifact, and
   if the control signal indicates that the adaptive filtering is not to be performed, omit the adaptive filtering of the biosignal when processing the biosignal.

7. An apparatus for measuring a biosignal, the apparatus comprising:
   a first electrode configured to measure the biosignal;
   a second elctrode configured to detect the biosignal;
   at least one processor configured to
      obtain a replication signal from the biosignal using the first electrode and the second electrode,
      wherein the replication signal is proportional to a motion artifact in the biosignal;
      determine, based on the replication signal, an artifact degree of the motion artifact;
      compare the artifact degree to a threshold to generate a comparison result;
      generate, based on the comparison result, a control signal controlling adaptive filtering of the biosignal to reduce the motion artifact in the biosignal; and
      process the biosignal based on the control signal.

8. The apparatus of claim 7, wherein the processor is configured to obtain the replication signal from the biosignal by measuring a change in impedance between the first electrode and the second electrode.

9. A method of measuring a biosignal, the method comprising:
   measuring the biosignal using a biosignal interface;
   detecting a dummy signal using a dummy interface;
   obtaining a replication signal from the biosignal using the biosignal interface and the dummy interface,
   wherein the replication signal is proportional to a motion artifact in the biosignal;
   determining, based on the replication signal, an artifact degree of the motion artifact;
   comparing the artifact degree to a threshold;
   generating, based on the comparison result, a control signal controlling adaptive filtering of the biosignal to reduce the motion artifact; and
   processing the biosignal based on the control signal.

10. The method of claim 9, wherein the obtaining of the replication signal from the biosignal comprises measuring a change a half cell potential between the biosignal interface and the dummy interface.

11. The method of claim 9, wherein:
   the determining of the artifact degree comprises indexing the replication signal during a period of time; and
   the generating of the control signal comprises:
      if the artifact degree exceeds the threshold, processing the biosignal by performing the adaptive filtering to reduce the motion artifact in the, and
      if the artifact degree does not exceed the threshold, omit the adaptive filtering of the biosignal during processing of the biosignal.

12. The method of claim 9, wherein the determining of the artifact degree comprises indexing a distribution of the replication signal, a root mean square of the replication signal, or an average magnitude of the replication signal during a time period.

13. The method of claim 9, wherein the processing of the biosignal comprises filtering the biosignal to reduce the motion artifact, using the replication signal.

14. A non-transitory computer-readable medium storing instructions that, when executed by a processor, cause the processor to perform the method of claim 9.

15. The method of claim 9, wherein the generating of the control signal comprises:

if the comparison result indicates that the artifact degree exceeds the threshold, generating the control signal to indicate that the adaptive filtering is to be performed; and if the comparison result indicates that the artifact degree does not exceed the threshold, generating the control signal to indicate that the adaptive filtering is not to be performed.

* * * * *